(12) United States Patent
Bernutz et al.

(10) Patent No.: US 10,198,931 B2
(45) Date of Patent: Feb. 5, 2019

(54) METHOD FOR SENDING AN ALARM TO PERSONS

(71) Applicant: Drägerwerk AG & Co. KGaA, Lübeck (DE)

(72) Inventors: Marco Bernutz, Mönkhagen (DE); Birger Landwehr, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 15/745,202

(22) PCT Filed: Jul. 1, 2016

(86) PCT No.: PCT/EP2016/001131
§ 371 (c)(1),
(2) Date: Jan. 16, 2018

(87) PCT Pub. No.: WO2017/012696
PCT Pub. Date: Jan. 26, 2017

(65) Prior Publication Data
US 2019/0012899 A1 Jan. 10, 2019

(30) Foreign Application Priority Data
Jul. 17, 2015 (DE) .................. 10 2015 009 087

(51) Int. Cl.
*H04W 4/90* (2018.01)
*G08B 21/02* (2006.01)
*G08B 25/00* (2006.01)
*G08B 25/01* (2006.01)
*G16H 40/20* (2018.01)

(52) U.S. Cl.
CPC ............ *G08B 25/001* (2013.01); *G08B 21/02* (2013.01); *G08B 25/016* (2013.01); *G16H 40/20* (2018.01); *H04W 4/90* (2018.02)

(58) Field of Classification Search
CPC .. G08B 25/001; G08B 25/005; G08B 25/016; G08B 25/006; G08B 13/1427; G08B 21/0247; G08B 25/008; G08B 27/00
See application file for complete search history.

(56) References Cited

U.S. PATENT DOCUMENTS 7,439,856 B2 10/2008 Weiner et al.
8,890,685 B1 11/2014 Sookman et al.
(Continued)

FOREIGN PATENT DOCUMENTS

WO 2004/070562 A2 8/2004

*Primary Examiner* — Omeed Alizada
(74) *Attorney, Agent, or Firm* — McGlew and Tuttle, P.C.

(57) ABSTRACT

A method sends an alarm to persons (P1, P2, P3, P4, P5), who are located in an area of a warning device (1, 2, 3, 4, 5), as a function of request signals (S1, S2) of at least one alarm source (10, 11). Each warning device specifies current countdowns (S1C1, S1C2, S1C3, S1C4, S1C5, S2C1, S2C2, S2C3, S2C4, S2C5) for each alarm source. When a request signal is sent by one of the alarm sources, the corresponding countdowns of all warning devices that receive the request signal are started. The warning device, with a countdown that has come to an end, sends an alarm signal (S1A1, S1A2, S1A3, S1A4, S1A5, S2A1, S2A2, S2A3, S2A4, S2A5). A manual acceptance of the sent alarm signal by a person, who is located in the area of the warning device that sends the alarm signal, ends the started countdowns of the other warning devices.

17 Claims, 1 Drawing Sheet

(56) References Cited

U.S. PATENT DOCUMENTS

2007/0013511 A1 1/2007 Weiner et al.
2008/0249386 A1 10/2008 Besterman et al.
2011/0279269 A1 11/2011 Gerber
2013/0293372 A1 11/2013 Philip et al.
2015/0154847 A1 6/2015 Oliver et al.

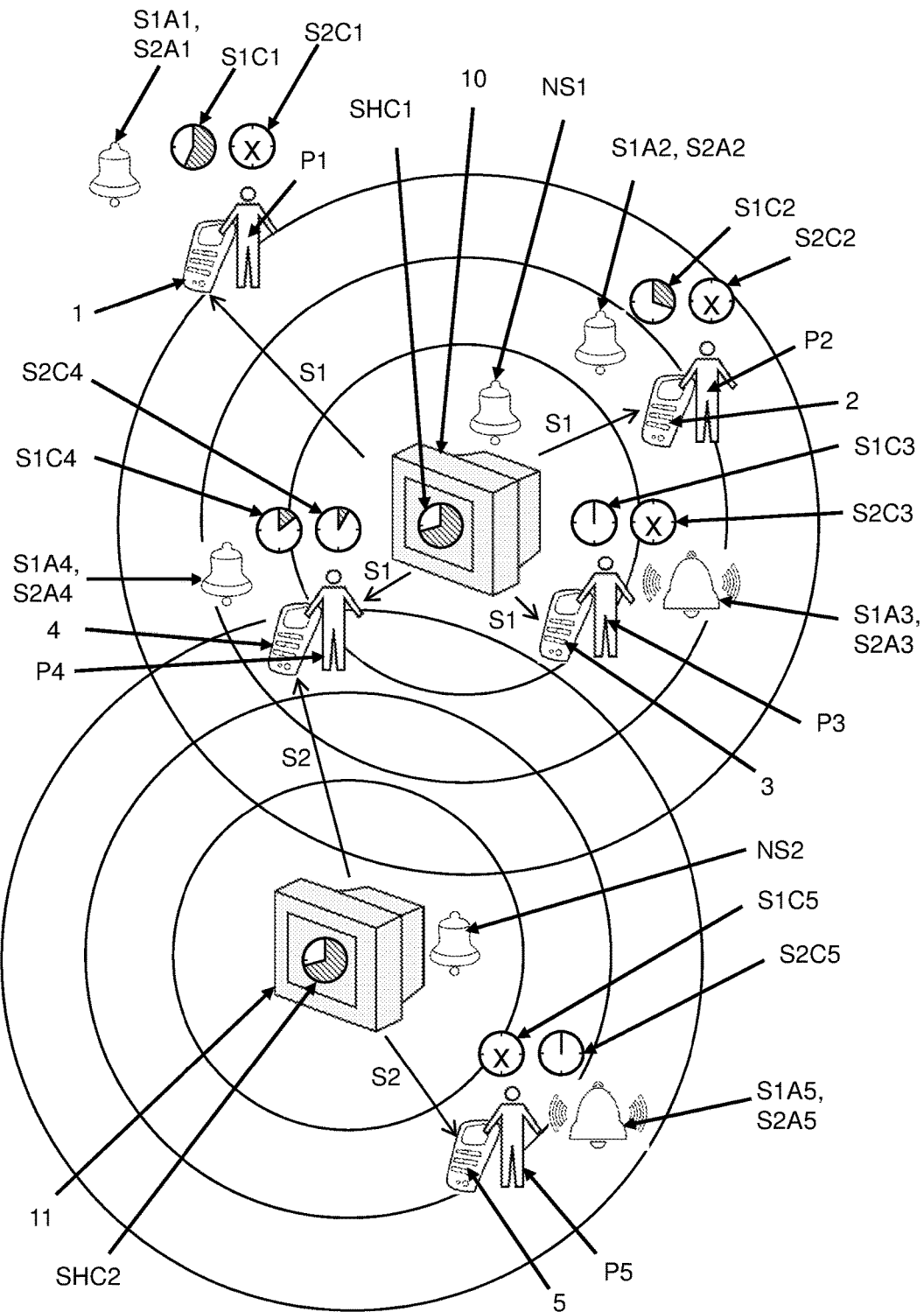

METHOD FOR SENDING AN ALARM TO PERSONS

CROSS REFERENCE TO RELATED APPLICATIONS

This application is a United States National Phase Application of International Application PCT/EP2016/001131, filed Jul. 1, 2016, and claims the benefit of priority under 35 U.S.C. § 119 of German Application 10 2015 009 087.9, filed Jul. 17, 2015 the entire contents of which are incorporated herein by reference.

FIELD OF THE INVENTION

The present invention pertains to a method for sending an alarm to persons, who are located in the area of a warning device, for example, in the area of health care staff.

BACKGROUND OF THE INVENTION

Such methods are employed to provide at least one person when an alarm is triggered to eliminate the event triggering the alarm, e.g., to call a member of the health care staff to a patient. It is a challenge in this connection that a person shall be provided as quickly as possible, without the persons developing alarm fatigue due to constant alarms, which they cannot look after or which has already been taken care of by other persons.

It is known, for example, from U.S. Pat. No. 7,439,856 B2 that an alarm can be sent to persons by means of a central alarm server step by step according to an escalation level plan by means of activating a warning device until a person takes care of the alarm event in question. The escalation level plan classifies the persons according to patient name, patient location, medical condition and reason for alarm for the patient, the availability of additional persons and their combinations. A certain person or group of persons is then sent an alarm first and persons who are less qualified are subsequently sent an alarm step by step if the aforementioned persons to whom an alarm has been sent do not take care of the alarm event.

It is disadvantageous here that the entire escalation is performed by the alarm server. However, a permanent connection to the warning devices is necessary for this, because these warning devices must be able to be reached by the server at any time at the moment of sending an alarm. However, precisely hospitals cover a large area and at times they are also shielded against radiation. Therefore, it frequently happens that the next warning device in the escalation cannot be reached precisely when an alarm is being sent to it. Nevertheless, the person assigned to the warning device is actually ready at this moment to take care of the alarm event. However, due to this person not being able to be reached, the next person in the escalation is sent an alarm, who can process the alarm event less efficiently, for example, because she must walk a longer distance or is less qualified.

SUMMARY OF THE INVENTION

An object of the present invention is to send alarms to responsible persons, e.g., health care staff, as purposefully and reliably as possible and thus to achieve high efficiency in the processing of alarms and to counteract alarm fatigue.

The present invention therefore pertains to a method for sending an alarm to persons who are located in the area of a warning device as a function of request signals from at least one alarm source, wherein each warning device specifies (especially independently) current countdowns for each of the alarm sources. When a request signal is sent from one of the alarm sources, the corresponding countdowns of all warning devices that receive the request signal are started. The warning device, whose started countdown comes to an end, sends an alarm signal. The manual acceptance of a sent alarm signal by a person who is located in the area of the warning device that sends the alarm signal interrupts the started countdown of the other warning devices, which are especially reset to start hereby.

Thus, alarm signals are not signaled simultaneously by all possible warning devices, but delayed according to the lengths of the countdowns and escalated staggered in time, especially until a person takes care of the event. The persons receive, on the whole, fewer alarm signals in this manner, as a result of which alarm fatigue is reduced. However, to alert a person to the alarm signal, it should not be, in particular, exclusively an acoustic and/or visual and/or tactile signal. Furthermore, alarm signals may comprise text messages as well as context information, which are displayed to the user.

Coordination of the escalation on the part of the alarm source is not necessary. The escalation is already set at the moment at which the request signal is sent based on the recognition of an alarm condition and is processed above all by the warning devices themselves. It is not even necessary for the warning devices to confirm the start of the countdown or the receipt of the request signal. High compatibility develops with different alarm sources, without a central alarm server being necessary.

Another advantage is that the countdowns according to the present invention continue to run even when the warning device is moving into a dead zone, in which it cannot be reached for a short time. As a result, a person can be sent an alarm by the warning device at this moment despite the lack of radio contact. Even if the manual acceptance cannot be sent out for a short time, this usually still happens during the other countdowns, because the person with the warning device will start moving in order to take care of the alarm event.

Conversely, it is not absolutely necessary for all warning devices to immediately receive the request signal even when the countdowns start. It is sufficient if the request signal is received within a defined time period. A warning device should preferably drop out of the escalation level plan and the still running longer countdowns should be shortened only when a warning device fails to send an optional confirmation over a time longer than the defined time period. Once a person has confirmed an alarm signal at the warning device, this confirmation is preferably limited in time. It can be ensured hereby that the alarm source will independently send an alarm signal of its own after a certain time if the person notified does not come to the alarm source or to the patient or does so only with a delay and does not eliminate the cause.

The specification of the countdowns by the warning devices also includes a blocking of the countdown against starting or, as an alternative, the raising of the countdown to the value infinite if the warning device shall not participate in the escalation of an alarm source, for example, because of an excessively great distance or because of lack of qualification of the person assigned to the warning device.

According to a more specific embodiment of the method, provisions are made for at least one of the warning devices to be a portable wireless warning device, which is carried along by one of the persons. The method is thus also suitable for sending an alarm to persons acting in a mobile manner. The portable wireless warning devices are connected to the alarm source or alarm sources especially in a wireless manner, especially indirectly or directly.

Conversely, there also is an option that the method is complemented to the effect that at least one of the warning devices is a stationary warning device, which sends an alarm to persons located in the local surrounding area. For example, persons in on-call rooms or at the reception can thus be sent an alarm.

According to a specific embodiment of the method, the manual rejection of an alarm signal by a person who is located in the area of the warning device that sends an alarm signal reduces the countdown of the other warning devices preferably by the time period of the still running shortest countdown. Consequently, if an alarm is rejected, the next warning device is activated more rapidly or immediately and this warning device sends an alarm signal.

Because the sending of a request signal at the alarm source usually characterizes an immediate need for action, an addition to the method makes provisions for the shortest countdown to equal zero for each alarm source and for the warning device or the warning devices containing this shortest countdown to immediately send an alarm signal when they receive a request signal.

The advantages of the method become especially clear in variants in which at least two alarm sources are present and a code of the triggering alarm source is added to each sent request signal. The warning devices then organize the countdown lengths of the escalation in small groups for each alarm source. For this they exchange information with one another indirectly or directly within the small groups. A plurality of alarm sources can send requests to persons independently from one another in this manner. The escalations now run independently according to the respective countdown lengths. Especially patient bells, mobile emergency call devices (also mobile telephones), fans, anesthesia devices, monitors, syringe pumps or software, e.g., on an alarm server, may be considered alarm sources.

Provisions are made in a more specific embodiment of the method for the alarm sources and the warning devices to communicate each exclusively with an alarm management server. As a result, the information infrastructure can be simplified. In addition, it is also possible to integrate out-of-house devices, e.g., mobile telephones. In particular, a central control device is created with the server. Different devices can be integrated with the server through a central interface. Different data transfer protocols of the warning devices and alarm sources can then be converted by the server, as a result of which compatibility develops. In addition, parameters for the length of the countdown can be set centrally and do not need to be set at the alarm source. The alarm source must therefore only be suitable for merely sending a request signal. The requirements imposed on the system for detecting the parameters are satisfied centrally. Training can also be carried out more simply at the server than, for example, in hospital rooms. In addition, access authorizations to the servers can be specified.

Moreover, alarm management servers offer the following advantageous possibilities:
  Interpretation of request signals and vital data of the patient, which arrive from the alarm source, in order to prioritize the forwarding of the request signals to the warning devices,
  generate new (multiparameter) alarm signals and to forward them,
  suppress the forwarding of the request signals to warning devices,
  replace individual request signals by new request signals (and the states thereof, e.g., "low airway pressure" becomes "patient can be disconnected from the ventilator"),
  consolidate alarm signals,
    by combining a plurality of request signals into an individual one based on knowledge of the context, and
    by assigning alarms that arrive from the same alarm source to the same period, e.g., no other persons shall be sent an alarm any more if a person has confirmed an alarm signal and more request signals are still coming from the same alarm source,
  request signals that come from the same alarm source should usually be assigned to the same person insofar as that person is responsible for it.

Provisions are made in a special embodiment variant of the method for the position of each warning device relative to each of the alarm sources to be determined and to be provided to the other warning devices, the lengths of the countdowns depending on the own position and the positions of the other warning devices relative to the alarm source for which the countdown is specified. It is thus possible to first send an alarm to persons located at certain locations. This can be embodied by fixed, especially single-time position specification in case of stationary warning devices. This can be embodied, for example, by field intensity determinations in WLAN networks, RFID information, barcode scanners, QR codes or user inputs in case of mobile warning devices.

According to another more specific embodiment, each warning device specifies its countdowns by taking into consideration the absolute distances or the walking distance from the warning device and the other warning devices to the location of use at which the corresponding alarm source is located. It is thus possible to first send an alarm to persons who have a short distance to walk to the location of use.

Furthermore, a method variant is provided, according to which each countdown is updated in real time or in a timed manner. It is thus possible to achieve a balance between the most accurate sending an alarm to persons possible and, for example, battery run times because power is consumed, in particular, for the data transfer. The countdowns may be implemented, for example, by sending a request signal to the warning devices, after which the warning devices receiving the request signal report back, especially by sending back an availability signal and/or by sending back a position signal.

In one modification of the method, each countdown is specified by taking into consideration the warning device, especially by taking into account the persons assigned to the warning device. It is thus possible, for example, to send an alarm to better qualified persons with a priority or else to trigger an alarm signal first in the staff room and at the mobile warning devices only thereafter.

The method may be complemented by a lack of availability being able to be entered at the warning device by a person, which is taken into consideration when specifying, especially updating, each countdown. The unavailable person is then not disturbed by an alarm signal and the escalation of the countdowns is not slowed down by persons who are not available anyway.

Comparable advantages are achieved if a warning device is considered to be unavailable for a defined time period after accepting an alarm signal, which is taken into consideration when specifying, especially updating, each countdown. A person who is currently in action will not then be disturbed by an additional alarm signal. This may be implemented either by not starting the countdown on the warning device or at least by prolonging the countdown to values that are greater than the countdowns of the other warning devices.

Moreover, provisions are made in a variant of the method for the alarm source to start, when a request signal is sent, a safety countdown, which is longer than the countdowns of the warning devices, which latter countdowns are started with the request signal, a request signal being again sent or an acoustic and/or visual and/or tactile alarm signal of its own being sent by the alarm source upon the end of the safety countdown. The situation in which the alarm event is not taken care of by any person is thus prevented from occurring.

Further, an expansion of the method is advantageous, in which it can be specified which of the warning devices are assigned to which of the alarm sources, and this is taken into consideration when specifying the countdowns. It can thus be specified which persons are suitable for taking care of an alarm event. For example, it can be specified for the alarm source which person is qualified and which person is not qualified.

Since the action has different requirements at each alarm source, it is advantageous if the countdowns can be specified and/or are specified individually in terms of their lengths for each alarm sources.

Strategies for optimizing the load and also for relieving the clinical staff can be implemented based on another variant. In particular, a redistribution of the request signals among all warning devices can be performed by an analysis performed to determine how often a person has taken care of alarm signals compared to the other persons. The accepted request signals of the alarm signals triggered at the warning device as well as the alarm signals confirmed by the corresponding person are stored and analyzed here in each warning device. The countdowns of the persons with few instances of acceptance are correspondingly shortened based on the assessment or the countdowns are prolonged for the persons frequently accepting request signals.

Provisions are made in a special embodiment for the countdowns of at least two warning devices as well as for the same alarm source to be equal. Two persons can thus be addressed at the same time. This is especially helpful in case care by a team is necessary or in case an alarm has an especially high priority. The shortest countdown in a hospital should be as short as possible and the longest countdown should be as long as clinically acceptable. Further features, details and advantages of the present invention appear from the text of the claims as well as from the following description of an exemplary embodiment on the basis of a drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:
FIG. 1 is a schematic view of persons with warning devices in the area around two alarm sources.

DESCRIPTION OF THE PREFERRED EMBODIMENTS

Referring to the drawings, FIG. 1 shows a schematic view of five persons P1, P2, P3, P4, P5, who each carry along a respective warning device 1, 2, 3, 4, 5, in the area of two alarm sources 10, 11. The warning devices 1, 2, 3, 4, 5 are portable wireless warning devices, which are connected to the alarm sources 10, 11 in a wireless manner. Three respective rings around the alarm sources 10, 11 symbolize a classification of the warning devices 1, 2, 3, 4, 5 according to the walking distance from these. Persons P1, P2, P3, P4, P5 outside the rings are too far away from the respective alarm source 10, 11. They are not available for accepting a request signal S1, S2.

Furthermore, it is seen that two clocks with a respective countdown S1C1, S1C2, S1C3, S1C4, S1C5 each are assigned to each person. These are started by the warning devices 1, 2, 3, 4, 5 when they receive, as is shown, a request signal S1, S2. It is seen that the first warning device 1 has received a first request signal and a first countdown S1C1 is running. Should the first countdown S1C1 come to an end, an alarm signal S1A1 would be triggered. The first warning device 1 is located outside the radius of responsibility of the second alarm source 11, so that no second countdown S2C1 was started. It is thus also impossible for a potential alarm signal S2A1 to be triggered in the shown position of the first person P1.

The second warning device 2 has received a first request signal S1 and a first countdown S1C2 is running. Should the first countdown S1C2 come to an end, an alarm signal S1C2 would be triggered. The second warning device 2 is located outside the radius of responsibility of the second alarm source 11, so that no second countdown S2C2 was started. It is thus also impossible to trigger a potential alarm signal S2A2 in the shown position of the second person P2.

The third warning device 3 has received a first request signal S1 and a first countdown S1C3 has come to an end. However, the third warning device 3 is located outside the radius of responsibility of the second alarm source 11, so that no second countdown S2C3 was started. Countdown S1C3, which has come to an end, has triggered an alarm signal S1A3, which can now be accepted or rejected by the third person P3. A code is attached to the alarm signal S1A3, so that it can be distinguished by the third person 3 from a potential alarm signal S2A3, which could be triggered by the second countdown S2C3.

The fifth warning device 5 has received a second request signal S2 and a second countdown S2C5, which has triggered an alarm signal S2A5, has thereupon come to an end. The fifth warning device 5 is located outside the radius of responsibility of the first alarm source 10, so that no first countdown S1C5 was started. It is thus also impossible for a potential alarm signal S1A5 to be triggered in the shown position of the first person P5.

The fourth warning device 4 has received a first request signal S1 and a second request signal S2 and a first countdown S1C4 as well as a second countdown S2C4 are running. Should the first countdown S1C4 come to an end, an alarm signal S1A4 would be triggered. Should the second countdown S2C4 come to an end, which has already advanced farther, an alarm signal S2A4 is, however, triggered. Should the third person P3 accept her alarm signal S1A3, the first countdown S1C4 is interrupted. If the fifth person P5 accepts the triggered alarm signal S2A5, the second countdown S2C4 is interrupted.

Alarm signals S1A3, S1A4, S1A2, S1A1 are then triggered by the first request signal S1 in a chronological sequence at the third person P3, then at the fourth person P4, then at the second person P2 and at the first person P1 as the last person. A first safety countdown SHC1 is also running at the first alarm source 10 for safety. This countdown is longer than the first countdowns S1C1, S1C2, S1C3, S1C4, and a first request signal S1 is again sent when it ends in order to reach all available warning devices 1, 2, 3, 4, 5, which are now within the range of responsibility of the first alarm source 10, and to start a new escalation by starting the first countdowns S1C1, S1C2, S1C3, S1C4, S1C5. In addition or as an alternative, the first alarm source 10 may optionally send an acoustic, visual and/or tactile alarm signal NS1 of its own.

Concerning the second alarm source 11, alarm signals S2A5, S2A4 are sent in chronological sequence at the fifth person P5 and then at the fourth person P4. A safety countdown SHC2 is also running at the second alarm source 11 for safety. When this countdown comes to an end, the second alarm source 11 repeatedly sends a second request signal S2 in order to reach all available warning devices 1, 2, 3, 4, 5, which are then in the range of availability of the second alarm source 11, and to start a new escalation by starting the second countdowns S1C1, S1C2, S1C3, S1C4, S1C5. In addition or as an alternative, the second alarm source 11 may optionally send an acoustic, visual and/or tactile alarm signal NS2 of its own.

A method for sending an alarm to the persons P1, P2, P3, P4, P5, who are located in the area of the warning devices 1, 2, 3, 4, 5, can consequently be carried out with these circumstances as a function of the request signals S1, S2 from the two alarm sources 10, 11, in which method each warning device 1, 2, 3, 4, 5 specifies current countdowns S1C1, S1C2, S1C3, S1C4, S1C5, S2C1, S2C2, S2C3, S2C4, S2C5 for each of the alarm sources 10, 11. The first, second and third warning devices 1, 2, 3 have blocked here the second countdown S2C1, S2C2, S2C3 because they are too far away from the second alarm source 11. The warning devices 1, 2, 3, 4, 5 either determine the position outside the zone around the alarm source 10, 11 themselves, or the warning devices 1, 2, 3, 4, 5 receive a request signal within the zone to specify the countdown S1C1, S1C2, S1C3, S1C4, S1C5, S2C1, S2C2, S2C3, S2C4, S2C5 and none outside the zone.

To specify the countdowns S1C1, S1C2, S1C3, S1C4, S1C5, S2C1, S2C2, S2C3, S2C4, S2C5, the own position relative to each of the alarm sources 10, 11 should be determined by each warning device 1, 2, 3, 4, 5 and provided for the other warning devices 1, 2, 3, 4, 5. The length of the countdown S1C1, S1C2, S1C3, S1C4, S1C5, S2C1, S2C2, S2C3, S2C4, S2C5 is then specified as a function of the own position and the positions of the other warning devices 1, 2, 3, 4, 5 relative to the alarm source 10, 11.

In particular, each warning device 1, 2, 3, 4, 5 should specify its countdowns S1C1, S1C2, S1C3, S1C4, S1C5, S2C1, S2C2, S2C3, S2C4, S2C5 by taking into consideration the absolute distances or the walking distance in space of the warning device 1, 2, 3, 4, 5 and of the other warning devices 1, 2, 3, 4, 5 from the location of use of the corresponding alarm source 10, 11.

The person P1, P2, P3, P4, P5 assigned to the warning device 1, 2, 3, 4, 5 comes into consideration as an additional parameter for specifying the countdowns S1C1, S1C2, S1C3, S1C4, S1C5, S2C1, S2C2, S2C3, S2C4, S2C5 in order to take his qualification, responsibility and function adequately into account during the escalation. Each countdown S1C1, S1C2, S1C3, S1C4, S1C5, S2C1, S2C2, S2C3, S2C4, S2C5 may be updated in real time or in a timed manner.

Furthermore, there is an option for the possibility for a person P1, P2, P3, P4, P5 to input a lack of availability at the warning device 1, 2, 3, 4, 5, which is taken into consideration at the time of specifying and especially at the time of updating each countdown S1C1, S1C2, S1C3, S1C4, S1C5, S1C1, S2C2, S2C3, S2C4, S2C5. This may also comprise a general unavailability of certain persons P1, P2, P3, P4, P5 for certain tasks or alarm sources 10, 11.

Further, a warning device 1, 2, 3, 4, 5 may the considered to be unavailable for a defined time period after accepting an alarm signal S1A1, S1A2, S1A3, S1A4, S1A5, S2A1, S2A2, S2A3, S2A4, S2A5, which is taken into consideration when specifying, especially when updating each countdown S1C1, S1C2, S1C3, S1C4, S1C5, S2C1, S2C2, S2C3, S2C4, S2C5.

At the time of the shown sending of a request signal S1, S2 by one of the alarm sources 10, 11, the corresponding countdowns S1C1, S1C2, S1C3, S1C4, S1C5, S2C1, S2C2, S2C3, S2C4, S2C5 of all warning devices 1, 2, 3, 4, 5, which receive the request signal S1, S2, are started. The warning device 1, 2, 3, 4, 5, whose started countdown S1C1, S1C2, S1C3, S1C4, S1C5, S2C1, S2C2, S2C3, S2C4, S2C5 is running, sends an alarm signal S1A1, 51A2, 51A3, 51A4, 51A5, S2A1, S2A2, S2A3, S2A4, S2A5.

In case of manual acceptance of a sent alarm signal S1A1, S1A2, S1A3, S1A4, S1A5, S2A1, S2A2, S2A3, S2A4, S2A5 by the person P1, P2, P3, P4, P5, who is located in the area of the warning device 1, 2, 3, 4, 5, which sends the alarm signal S1A1, S1A1, S1A3, S1A4, S1A5, S2A1, S2A2, S2A3, S2A4, S2A5, the started countdowns S1C1, S1C2, S1C3, S1C4, S1C5, S2C1, S2C2, S2C2, S2C3, S2C4, S2C5 of the other warning devices 1, 2, 3, 4, 5 are terminated and reset to start.

If, for example, the third or fifth person P3, P5 now manually rejects the triggered alarm signals S1A3, S2A5, the countdowns S1C1, S1C2, S1C4, S2C4 of the other warning devices 1, 2, 4 are reduced, namely, especially each by the duration of the still running shortest countdown S1C4, S2C4.

It cannot be seen whether the shortest countdown S1C3, S2C5 in FIG. 1 had the zero value already at the start for each alarm source 10, 11, so that the warning devices 3, 5 containing the shortest countdowns S1C3, S2C3 have immediately sent the alarm signal S1A3, S2A5 when they received the request signal S1, S2. This is, however, optionally foreseeable. The alarm signals S1A3, S2A5 may be acoustic and/or visual and/or tactile signals. These also contain, in particular, information on which of the alarm sources the triggered alarm signals S1A3, S2A5 belong to. This is preferably brought about by means of a display. The display may optionally also show how many warning devices are still contained in the escalation level plan of a primary alarm source 10, 11, for example, by indicating 10: 4; 11: 2 on the first warning device 1;

which warning devices are still contained in the escalation level plan of a primary alarm source 10, 11, for example, by indicating 10: 1, 2, 3, 4; 11: 4, 5 on the first warning device 1;

in what order the escalation of the warning devices is arranged in the escalation level plan of a primary alarm source 10, 11, for example, by indicating 10: 3, 4, 2, 1; 11: 5, 4 on the first warning device 1; and what the status of the other warning devices 1, 2, 3, 4, 5 is, for example, by indicating 10: ((3)), 4, 2, 1, x5x; 11: ((5)), 4, x1x, x2x, x3x, on the first warning device 1. The parentheses symbolize an alarm signal sending, and the x-es symbolize a lack of availability.

The present invention is not limited to one of the above-described embodiments but may be varied in many different ways.

All the features and advantages appearing from the claims, the description and the drawing, including design details, arrangements in space and method steps, may be essential for the present invention both in themselves and in the many different combinations. While specific embodiments of the invention have been shown and described in detail to illustrate the application of the principles of the invention, it will be understood that the invention may be embodied otherwise without departing from such principles.

The invention claimed is:

1. A method of sending an alarm, the method comprising the steps of:
   providing a plurality of warning devices with countdown timers having different lengths;
   generating an alarm request signal; each of the plurality of warning devices receiving the alarm request signal;
   the each of the plurality of warning devices starting their respective countdown timers when the alarm request signal is received;
   the each warning device generating an alarm signal when a respective countdown has finished;
   the each of the plurality of warning devices being configured to selectively take responsibility for the alarm request signal;
   each of the plurality of warning devices stopping their respective countdown timers when one warning device takes responsibility for the alarm request signal.

2. A method of sending an alarm in accordance with claim 1, further comprising: providing at least one of the warning devices as a portable wireless warning device; and one person carrying the portable wireless warning device.

3. A method of sending an alarm in accordance with claim 1, further comprising: one of the plurality of warning devices manually rejecting the alarm signal; reducing the length of another one of the countdown timers after the one warning device performs said manually rejecting of the alarm signal.

4. A method of sending an alarm in accordance with claim 1, wherein: the length of the countdown timer of one of the plurality of warning devices equals zero.

5. A method of sending an alarm in accordance with claim 1, further comprising: providing a plurality of alarm sources, each of the plurality of alarm sources being configured to generate an alarm request signal with a code identifying the respective one of the plurality of alarm sources.

6. A method of sending an alarm in accordance with claim 5, wherein: the plurality of alarm sources and the plurality of warning devices communicate each exclusively with one alarm management server.

7. A method of sending an alarm in accordance with claim 1, further comprising: providing an alarm source; determining a position of the each warning device relative to the alarm source; setting a length of each of the countdown timers as a function of the position of the respective warning device relative to the alarm source.

8. A method of sending an alarm in accordance with claim 1, further comprising: providing an alarm source; determining a distance of the each warning device relative to the alarm source; setting a length of each of the countdown timers as a function of the distance of the respective warning device relative to the alarm source.

9. A method of sending an alarm in accordance with claim 5, further comprising: updating the length of each of the plurality of countdown timers is in real-time or in a timed manner.

10. A method of sending an alarm in accordance with claim 5, wherein: the plurality of warning devices include a plurality of different types of warning devices; the length of each of the plurality of countdown timers is dependent upon the respective type of the warning device.

11. A method of sending an alarm in accordance with claim 5, further comprising: configuring each of the plurality of warning devices to indicate availability; setting the lengths of the countdown timers dependent upon the availability of the each of the plurality of warning devices.

12. A method of sending an alarm in accordance with claim 11, further comprising: one of the plurality of warning devices taking responsibility for the alarm request signal; indicating that the one of the plurality of warning devices is unavailable for a defined time period after said taking responsibility for the alarm request signal.

13. A method of sending an alarm in accordance with claim 1, further comprising: starting a safety countdown with said generating of the alarm request signal, a length of said safety countdown being longer than the length of the plurality of countdown timers; generating another alarm request signal when the safety countdown has finished.

14. A method of sending an alarm in accordance with claim 1, further comprising: providing a plurality of alarm sources; selectively assigning each of the plurality of warning devices to one of the plurality of alarm sources; selectively setting a length of the countdown timers of each of the plurality of warning devices dependent upon the alarm source that the respective warning device is assigned to.

15. A method of sending an alarm in accordance with claim 9, wherein further comprising: setting an availability of one of the plurality of warning devices; updating a length of each of the countdown timers based on the availability of the one of the plurality of warning devices.

16. A method of sending an alarm in accordance with claim 9, wherein further comprising: one of the plurality of warning devices taking responsibility for the alarm request signal; indicating that the one of the plurality of warning devices is unavailable for a defined time period after said taking responsibility for the alarm request signal; updating a length of each of the countdown timers based on the unavailability of the one of the plurality of warning devices.

17. A method of sending an alarm in accordance with claim 1, further comprising: selectively setting a length of the countdown timers of the each of the plurality of warning devices depending on a characteristic of a respective warning device.

* * * * *